United States Patent
Nakanishi et al.

(10) Patent No.: US 7,123,691 B2
(45) Date of Patent: Oct. 17, 2006

(54) X-RAY COMPUTED TOMOGRAPHY SCANNER

(75) Inventors: Satoru Nakanishi, Utsunomiya (JP); Hiroyuki Kura, Nasushiobara (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 0 days.

(21) Appl. No.: 11/119,749

(22) Filed: May 3, 2005

(65) Prior Publication Data

US 2005/0254616 A1   Nov. 17, 2005

(30) Foreign Application Priority Data

May 13, 2004   (JP)   ............................. 2004-143526

(51) Int. Cl.
*H05G 1/28* (2006.01)
*H05G 1/00* (2006.01)

(52) U.S. Cl. ........................... 378/165; 378/162; 378/4

(58) Field of Classification Search ................. 378/4, 378/19, 20, 62, 108, 205, 162, 165
See application file for complete search history.

(56) References Cited

U.S. PATENT DOCUMENTS

| 5,212,717 A | 5/1993 | Hada |
| 2003/0016778 A1* | 1/2003 | Tachizaki et al. ............... 378/4 |
| 2003/0091157 A1* | 5/2003 | Nakanishi et al. .......... 378/205 |
| 2003/0099323 A1* | 5/2003 | Nagata et al. ................. 378/4 |
| 2004/0131139 A1* | 7/2004 | Oota et al. ..................... 378/4 |

FOREIGN PATENT DOCUMENTS

| EP | 1 396 229 A1 | 3/2004 |
| JP | 9-164135 | 6/1997 |

* cited by examiner

*Primary Examiner*—Edward J. Glick
*Assistant Examiner*—Irakli Kiknadze
(74) *Attorney, Agent, or Firm*—Oblon, Spivak, McClelland, Maier & Neustadt, P.C.

(57) ABSTRACT

An X-ray computed tomography scanner that performs helical scanning based on a designated scanning range and collects X-ray projection data, comprising a determination unit which determines an X-ray irradiation range necessary for reconstructing an image within the scanning range, and a display unit which displays an image formed by superimposing the X-ray irradiation range on a scanogram.

12 Claims, 3 Drawing Sheets

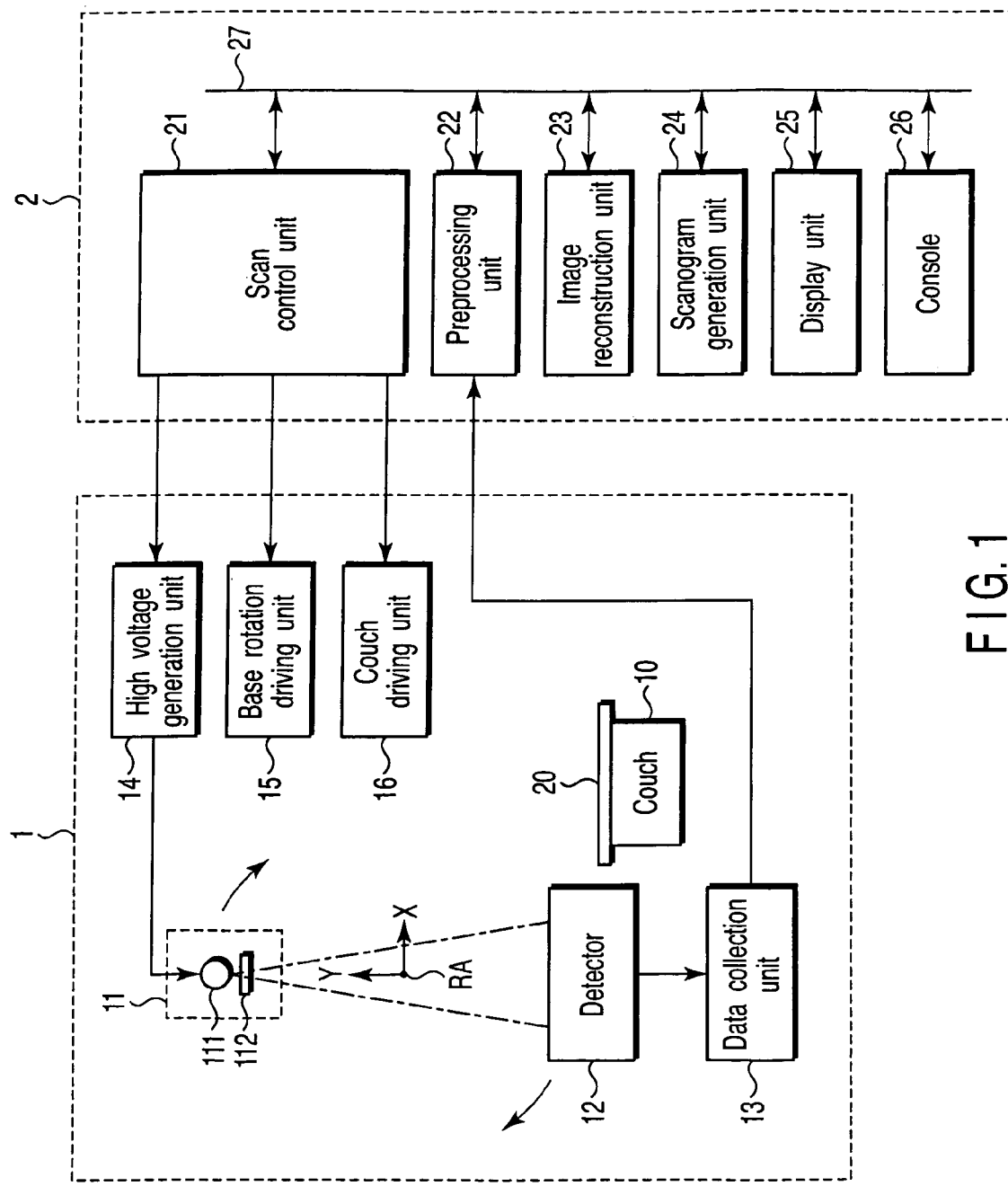
F I G. 1

X-RAY COMPUTED TOMOGRAPHY SCANNER

CROSS-REFERENCE TO RELATED APPLICATIONS

This application is based upon and claims the benefit of priority from prior Japanese Patent Application No. 2004-143526, filed May 13, 2004, the entire contents of which are incorporated herein by reference.

BACKGROUND OF THE INVENTION

1. Field of the Invention

The present invention relates to an X-ray computed tomography scanner for performing helical scanning.

2. Description of the Related Art

A function of setting a scanning range using a scanogram (X-ray transmission image) is known as one of functions of an X-ray computed tomography scanner (referred to as an X-ray CT scanner hereinafter) (see, for example, Jpn. Pat. Appln. KOKAI Publication No. 9-164135). This function is performed to set a range designated freely by a user on a scanogram as a scanning range. Using this function, the user can determine a scanning range visually and simply.

The scanning range set by the above function is a range within which an image should be captured by image reconstruction. In helical scanning, in order to capture an image in a certain position, the image needs to be interpolated by data before and after the position. Data is therefore collected from a range that is larger than the scanning range described above. In other words, the range of application of X-rays to a subject becomes larger than the above scanning range.

It is feared that a user who does not understand the above characteristic of the helical scanning will set a scanning range without considering that X-rays are applied outside a designated range.

BRIEF SUMMARY OF THE INVENTION

Under the foregoing circumstances, it is to be wished that a user should reliably recognize a range within which X-rays are actually applied.

According to an aspect of the present invention, there is provided an X-ray computed tomography scanner that performs helical scanning based on a designated scanning range and collects X-ray projection data, comprising: a determination unit which determines an X-ray irradiation range necessary for reconstructing an image within the scanning range; and a display unit which displays an image formed by superimposing the X-ray irradiation range on a scanogram.

According to anther aspect of the present invention, there is provided an X-ray computed tomography scanner that performs helical scanning based on a designated scanning range and collects X-ray projection data, comprising: a determination unit which determines an X-ray irradiation range necessary for reconstructing an image within the scanning range; and a generation unit which generates data of an image formed by superimposing the X-ray irradiation range on a scanogram.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram of the principal part of an X-ray CT scanner according to an embodiment of the present invention;

DETAILED DESCRIPTION OF THE INVENTION

Figure 2:
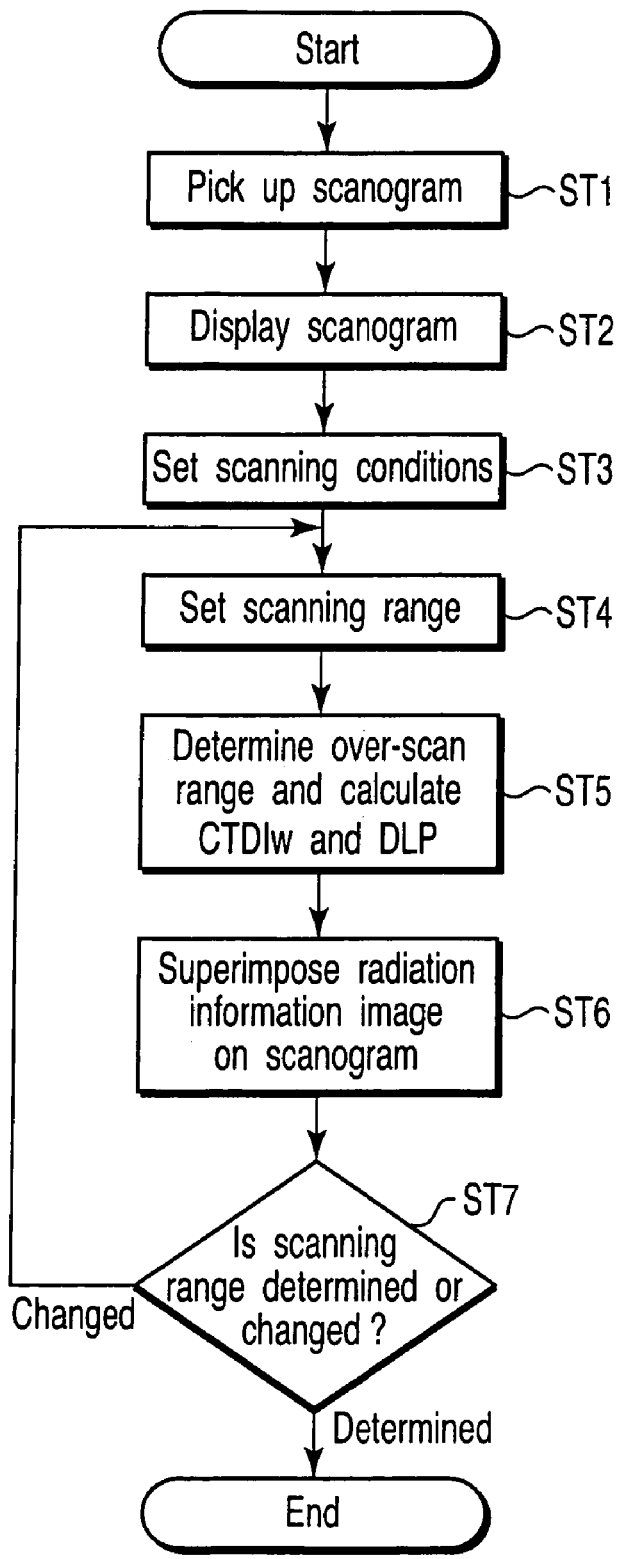
FIG. 2 is a flowchart of a procedure of a scan control unit of the X-ray CT scanner shown in FIG. 1 in a preparatory process.

An X-ray CT scanner according to an embodiment of the present invention will be described with reference to the accompanying drawings.

FIG. 1 is a block diagram of the principal part of the X-ray CT scanner according to the embodiment of the present invention. This X-ray CT scanner comprises a scan gantry 1 and a computer unit 2. The scan gantry 1 is a component for collecting projection data about a subject. The collected projection data is subjected to image reconstruction, real prep and the like in the computer unit 2.

The subject is inserted into a cavity (scanning hollow area) of the scan gantry 1 while being placed on a top plate 20 of a couch 10. The top plate 20 is driven by a couch driving unit 16 and moved in its longitudinal direction. The couch 10 is usually provided such that the longitudinal direction becomes parallel with a rotating axis RA (described later) which coincides with the body axis and the z-axis. The scan gantry 1 includes an annular rotating base (not shown) that is driven and rotated around the rotating axis RA by a base rotation driving unit 15. On the rotating base, an X-ray tube unit 11 and an X-ray detector 12 are mounted opposite to each other.

The X-ray tube unit 11 includes an X-ray tube 111 and an X-ray filter 112. The X-ray tube 111 radiates X-rays. The X-ray filter 112 eliminates low-energy components from the X-rays to reduce the radiation doses. An inverter-type high voltage generation unit 14 is provided to apply power to the X-ray tube unit 111. The unit 14 includes a high voltage transformer, a filament current generator and a rectifier. The unit 14 also includes a tube voltage selector and a filament current selector to control a tube voltage and a filament current freely or stage by stage.

The output of the X-ray detector 12 is supplied to the computer unit 2 via a data collection unit 13 and a slip ring (not shown). The slip ring allows the rotating base to rotate continuously.

The computer unit 2 includes a scan control unit 21, a preprocessing unit 22, an image reconstruction unit 23, a scanogram generation unit 24, a display unit 25 and a console 26. These units 21 to 26 are connected to each other through a data/control bus 27.

The scan gantry 1 supplies data to the computer unit 2. Then, the data is supplied to the image reconstruction unit 23 or the scanogram generation unit 24 through the preprocessing unit 22 as projection data. The projection data is used for reconstructing tomographic image data or generating scanogram data. The tomographic image data and scanogram data are displayed on the display unit 25. The scanogram data is also supplied to the scan control unit 21 and used for setting a scanning range of a tomographic image.

The console 26 is provided to input various information items and various instructions by an operator. The information items include scanning conditions and scanning ranges. The console 26 has an operating screen. A setting screen that is favorably elaborated such that the scan control unit 21 can assist the operator in inputting the above information items and instructions is displayed on the operating screen or the display unit 25.

The scan control unit 21 controls the respective units to perform scanning under preset conditions. The unit 21 has a determination function and a display control function and thus operates as a determination unit and a display control unit. The determination function is performed to determine an over-scan range (described later), while the display control function is done to display a radiation information image (describe later), which represents an over-scan range and the like, on the display unit 25.

An operation of the X-ray CT scanner so configured will be described. In particular, a procedure of the scan control unit 21 regarding a preparatory process in helical scanning will be described.

FIG. 2 is a flowchart of a procedure of the scan control unit 21 in the preparatory process.

In step ST1, the scan control unit 21 controls the respective units in order to pick up a scanogram. This control is performed by, e.g., a well-known procedure. In step ST2, the scan control unit 21 causes the display unit 25 to display the scanogram picked up in step ST1.

In step ST3, the scan control unit 21 sets conditions for picking up a tomographic image based on user's operations of the console 26. The conditions include a reconstruction condition and scanning conditions such as a helical pitch, the thickness of collected slices, the number of rows, the amount of movement of the couch per rotation, X-ray tube voltage, X-ray tube current, scanning time per rotation and a field of view (FOV). In step ST4, the scan control unit 21 sets a scanning range based on the user's operations of the console 26. The scanning range is a range within which a user is to pick up a tomographic image.

In step ST5, the scan control unit 21 determines an over-scan range in consideration of the conditions set in step ST3 and the scanning range set in step ST4, and computes a weighted computed tomography dose index 100 (CTDIw) and a dose length product (DLP). The over-scan range indicates a range that is scanned to acquire data for complementing data within the scanning range. Basically, the over-scan range depends on within which range data is required by the reconstruction process. However, there is a case where the over-scan range varies with the scanning conditions such as a helical pitch, the thickness of an image, the thickness of collected slices, the number of rows, and then amount of movement of the couch. The scan control unit 21 therefore determines the over-scan range in consideration of the conditions that affect the over-scan range. This determination can be performed by computations and with reference to a correspondence table. The CTDIw is an index of radiation doses in 10-mm thicknesses per rotation. The DLP indicates a total dose of radiation under the preset conditions.

Figure 3:
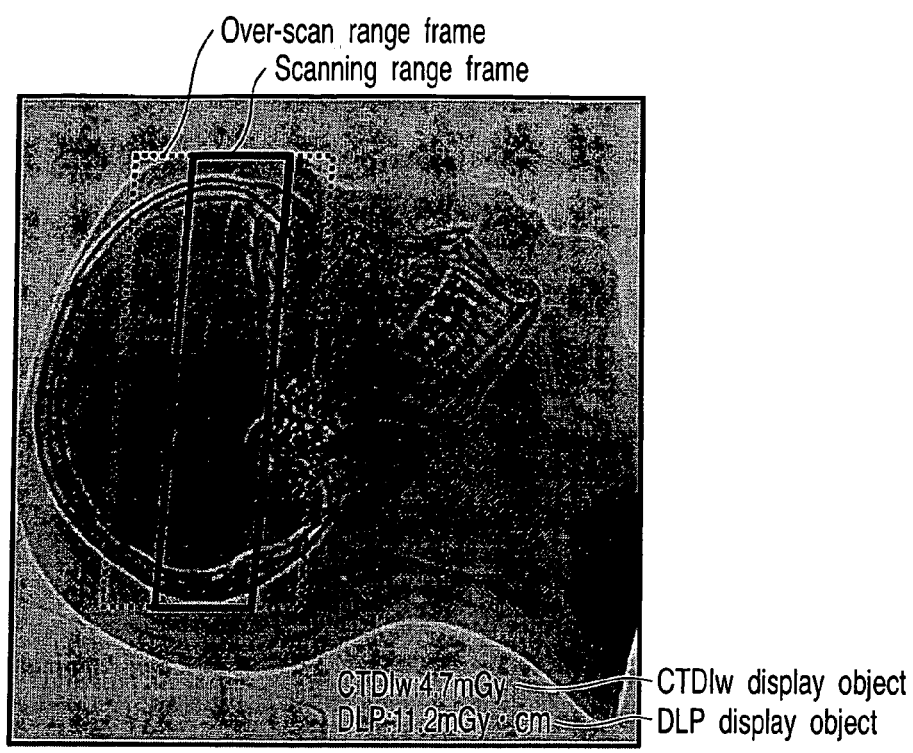
FIG. 3 is an illustration of an image formed by superimposing a radiation information image on a scanogram.

In step ST6, the scan control unit 21 superimposes a radiation information image on the scanogram and displays it. FIG. 3 shows an example of an image formed by the superimposition. As shown in FIG. 3, the radiation information image includes a scanning range frame, an over-scan range frame, a CTDIw display object and a DLP display object. The scanning range frame indicates the scanning range set in step ST4. The over-scan range frame indicates the over-scan range determined in step ST5. The CTDIw display object is a character string corresponding to the CTDIw computed in step ST4. The DLP display object is a character string corresponding to the DLP computed in step ST4. These range frames and display objects are marks that are created by computer graphics.

In step ST7, the scan control unit 21 confirms whether to determine or change the currently set scanning range. If the user changes the scanning range through the console 26, the scan control unit 21 shifts from step ST7 to step ST4 and performs the steps ST4 to ST6 again. If the user determines the scanning range through the console 26, the scan control unit 21 completes the process shown in FIG. 2.

According to the present embodiment described above, an operator can reliably and easily recognize a range within which X-rays are actually applied within the currently set scanning range based on the over-scan ranger frame superimposed on a scanogram. The operator can thus designate an appropriate scanning range in consideration of the irradiation range of X-rays.

The following modifications can be made to the present embodiment described above.

Figure 4:
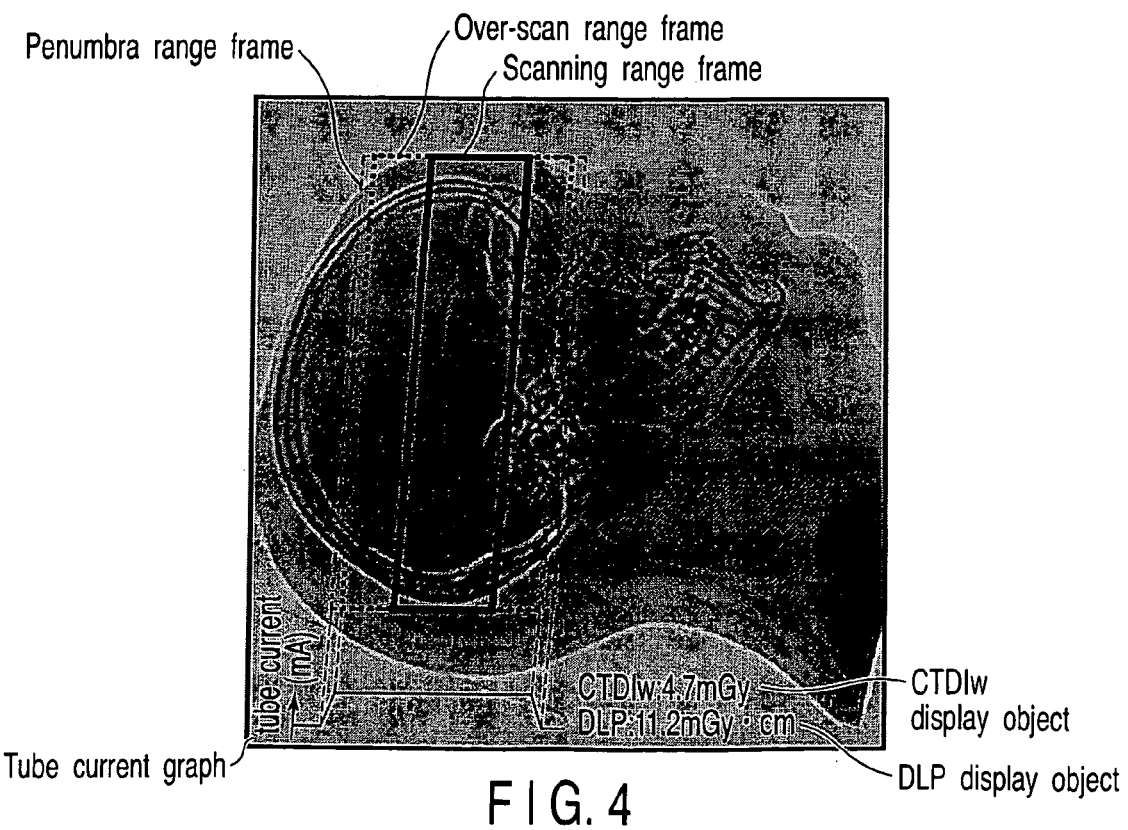
FIG. 4 is an illustration of an image formed by superimposing another radiation information image on the scanogram.

There is a case where a penumbra occurs outside the over-scan range and, in this case, a penumbra range frame indicative of the range of the penumbra can also be displayed as shown in FIG. 4. An operator can thus recognize the irradiation of X-rays by the penumbra. The penumbra range frame is a mark that is created by computer graphics.

The radiation doses in the penumbra are lower than that in the scanning range and the over-scan range. If a dose graph representing a difference in radiation doses is shown in FIG. 4, the operator can recognize the state of radiation more exactly. The scan control unit 21 computes radiation doses in the scanning range and the over-scan range. Since the penumbra range decreases in radiation doses with distance from the over-scan range, the scan control unit 21 computes a rate of the decrease. Based on the result of the computation, the unit 21 creates a dose graph representing the distribution of radiation doses as shown in FIG. 4. In FIG. 4, the radiation doses are represented by the amount of X-ray tube current. The radiation doses in the penumbra range can be computed as those in the center of the penumbra range or an average radiation dose within the penumbra range. Even though the dose graph is replaced with an image whose hue, saturation or lightness varies with the radiation doses inside each range frame or a contour line corresponding to the radiation doses inside each range frame, the same advantages can be obtained.

In FIG. 4, the amount of X-ray tube current is fixed during scanning. In contrast, there is a case where the amount of X-ray tube current varies with a position of a subject in its body axis direction during helical scanning. This technique is disclosed in, for example, Jpn. Pat. Appln. KOKAI Publication No. 2003-10168. The procedure disclosed in this Publication will be described briefly. First, a necessary amount of X-ray tube current is obtained in order to make an image standard deviation (SD) in each position in the body axis direction equal to a preset image SD based on a scanogram. Then, during helical scanning, an X-ray tube is driven by the X-ray tube current obtained in a scanning position. When such a process is performed, a dose graph that reflects variations in X-ray tube current is prepared and displayed.

The scanogram and the radiation information image can be displayed on a display unit externally added to the X-ray CT scanner.

The over-scan range in the above embodiment can be set to include a penumbra.

If the over-scan range does not vary so widely because of a difference in scanning conditions, it can be determined without considering the scanning conditions.

Only one of the CTDIw and DLP can be displayed, or another type of value regarding a radiation dose, such as CTDIvol can be displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography scanner that performs helical scanning based on a designated scanning range and collects X-ray projection data, comprising:
   a determination unit which determines a penumbra range and an X-ray irradiation range necessary for reconstructing an image within the scanning range; and
   a display unit which displays an image formed by superimposing a mark indicative of the scanning range, a mark indicative of the X-ray irradiation range, and a mark indicative of the penumbra range, on a scanogram.

2. The X-ray computed tomography scanner according to claim 1, wherein the determination unit determines the X-ray irradiation range in consideration of scanning conditions.

3. The X-ray computed tomography scanner according to claim 1, wherein the determination unit determines the X-ray irradiation range including a penumbra.

4. The X-ray computed tomography scanner according to claim 1, further comprising a calculation unit which computes a value of a radiation dose within the X-ray irradiation range, and
   wherein the display unit displays the value which is superimposed on the scanogram.

5. The X-ray computed tomography scanner according to claim 4, wherein the calculation unit computes at least one of a weighted computed tomography dose index 100 (CTDIw) and a dose length product (DLP).

6. The X-ray computed tomography scanner according to claim 1, further comprising a calculation unit which computes a value of a radiation dose within the X-ray irradiation range and a value of a radiation dose within the range of the penumbra, and
   wherein the display unit displays a difference between the values computed by the calculation unit in association with the mark indicative of the X-ray irradiation range and the mark indicative of the range of the penumbra.

7. An X-ray computed tomography scanner that performs helical scanning based on a designated scanning range and collects X-ray projection data, comprising:
   a determination unit which determines a penumbra range and an X-ray irradiation range necessary for reconstructing an image within the scanning range; and
   a generation unit which generates data of an image formed by superimposing a mark indicative of the scanning range, a mark indicative of the X-ray irradiation range, and a mark indicative of the penumbra range, on a scanogram.

8. The X-ray computed tomography scanner according to claim 7, wherein the determination unit determines the X-ray irradiation range in consideration of scanning conditions.

9. The X-ray computed tomography scanner according to claim 7, wherein the determination unit determines the X-ray irradiation range including a penumbra.

10. The X-ray computed tomography scanner according to claim 7, further comprising a calculation unit which computes a value of a radiation dose within the X-ray irradiation range, and
    wherein the generation unit generates data of an image formed by superimposing the X-ray irradiation range and the value on the scanogram.

11. The X-ray computed tomography scanner according to claim 10, wherein the calculation unit computes at least one of a weighted computed tomography dose index 100 (CTDIw) and a dose length product (DLP).

12. The X-ray computed tomography scanner according to claim 7, further comprising a calculation unit which computes a value of a radiation dose within the X-ray irradiation range and a value of a radiation dose within the range of the penumbra, and
    wherein the generation unit generates data of image indicating a difference between the values computed by the calculation unit in association with the mark indicative of the X-ray irradiation range and the mark indicative of the range of the penumbra.

* * * * *